United States Patent
Molleryd et al.

(10) Patent No.: US 10,927,344 B2
(45) Date of Patent: Feb. 23, 2021

(54) SEMI-STATIC CELL CULTURE

(71) Applicant: Cytiva Sweden AB, Uppsala (SE)

(72) Inventors: Karin Molleryd, Huddinge (SE);
Karin Wernersson, Uppsala (SE);
Sarah Marie Stone, Cardiff (GB);
Claudia Nune, Cardiff (GB); Rolf Kiessling, Stockholm (SE); Tanja Lovgren, Stockholm (SE); Lars Adamsson, Stockholm (SE); Ulrica Eistrand, Stockholm (SE)

(73) Assignee: Cytiva Sweden AB, Uppsala (SE)

( * ) Notice: Subject to any disclaimer, the term of this patent is extended or adjusted under 35 U.S.C. 154(b) by 98 days.

(21) Appl. No.: 15/574,003

(22) PCT Filed: May 27, 2016

(86) PCT No.: PCT/EP2016/062081
§ 371 (c)(1),
(2) Date: Nov. 14, 2017

(87) PCT Pub. No.: WO2016/189159
PCT Pub. Date: Dec. 1, 2016

(65) Prior Publication Data
US 2018/0291341 A1 Oct. 11, 2018

(30) Foreign Application Priority Data
May 28, 2015 (GB) ...................................... 1509202

(51) Int. Cl.
*C12N 5/0783* (2010.01)
*A61K 35/17* (2015.01)
*A61K 35/12* (2015.01)

(52) U.S. Cl.
CPC ............ *C12N 5/0636* (2013.01); *A61K 35/17* (2013.01); *A61K 2035/124* (2013.01); *C12N 2501/2302* (2013.01); *C12N 2501/2304* (2013.01); *C12N 2501/2307* (2013.01); *C12N 2501/2312* (2013.01); *C12N 2501/2315* (2013.01); *C12N 2501/2321* (2013.01); *C12N 2501/998* (2013.01); *C12N 2510/02* (2013.01); *C12N 2523/00* (2013.01); *C12N 2527/00* (2013.01)

(58) Field of Classification Search
CPC .......... C12N 5/0636; C12N 2501/2304; C12N 2501/2307; C12N 2501/2312; C12N 2501/2315; C12N 2501/2321; C12N 2501/998; C12N 2510/02; C12N 2527/00; C12N 2501/2302; A61K 35/17; A61K 2035/124
See application file for complete search history.

(56) References Cited

U.S. PATENT DOCUMENTS

2003/0036192 A1 2/2003 Singh
2003/0235908 A1 12/2003 Berenson et al.
2004/0110290 A1 6/2004 June et al.
2004/0224402 A1 11/2004 Bonyhadi et al.
2009/0233334 A1* 9/2009 Hildinger ............... C12M 23/14
435/71.1

FOREIGN PATENT DOCUMENTS

| EP | 2 116 556 A1 | 11/2009 |
|---|---|---|
| WO | 2003/024989 A2 | 3/2003 |
| WO | 2009/102697 A2 | 8/2009 |
| WO | 2010/093848 A1 | 8/2010 |
| WO | 2011/005773 A2 | 1/2011 |
| WO | 2013/088147 A1 | 6/2013 |

OTHER PUBLICATIONS

PCT International Search Report and Written Opinion for PCT Application No. PCT/EP2016/062081 dated Sep. 12, 2016 (12 pages).
GB Search Report for GB Application No. 1509202.6 dated Mar. 1, 2016 (4 pages).
Anonymous, "XuriTM. Believe in Better Futures," XP055296843, 2014, https://www.gelifesciences.com/gehcls_images/GELS/RelatedContent/Files/1400489554581/litdoc29107809201405252326 56.pdf.
Anonymous, "The Effect of Rocking Rate and Angle on T Cell Cultures Grown in Xuri(TM) Cell Expansion Systems," XP055253377, 2014, https://gelifesciences.com/gehcls_images/GELS/RelatedContent/Files/1411398823475/litdoc29116655201409222 31624.pdf.
Donia et al., "Simplified Protocol for Clinical-Grade Tumor-Infiltrating Lymphocyte Manufacturing with Use of the Wave Bioreactor," Cytotherapy, 2014, 16:1117-1120.
Labarrierre et al., "A Full GMP Process to Select and Amplify Epitope-Specific T Lymphocytes for Adoptive Immunotherapy of Metastatic Melanoma," Clinical and Development Immunology, 2003 (11 pages).
Sadeghi et al., "Large-Scale Bioreactor Expansion of Tumor-Infiltrating Lymphocytes," Journal of Immunological Methods, 2011, 364:94-100.
Somerville et al., "Bioreactors Get Personal," OncoImmunology, 2012, 1(8)1435-1437.
Somerville et al., "Clinical Scale Rapid Expansion of Lymphocytes for Adoptive Cell Transfer Therapy in tghe WAVE(R) Bioreactor," Journal of Translational Medicine, 2012, 10(69) (11 pages).
Vera et al., "Accelerated Production of Antigen-Specific T Cells for Preclinical and Clinical Applications Using Gas-Permeable Rapid Expansion Cultureware (G-Rex)," J. Immunother, 2010, 33(3):305-315.
Wang et al., "Manufacture of Tumor- and Virus-Specific T Lymphocytes for Adoptive Cell Therapies," Cancer Gene Ther., 2015, 22(2):85-94.
Japanese Office Action for JP Application No. 2017-559496 dated Jan. 14, 2020 (8 pages with English translation).

* cited by examiner

*Primary Examiner* — Taeyoon Kim
(74) *Attorney, Agent, or Firm* — Eversheds Sutherland (US) LLP

(57) ABSTRACT

The present invention relates to cell culture in bioreactors, such as flexible cellbag bioreactors. More specifically the present invention relates to methods for simplifying the production of clinically relevant cell products for use in cell therapy.

23 Claims, 7 Drawing Sheets

SEMI-STATIC CELL CULTURE

CROSS REFERENCE TO RELATED APPLICATIONS

This application claims the priority benefit of PCT/EP2016/062081 filed on May 27, 2016 which claims priority benefit of GB Application No. 1509202.6 filed May 28, 2015. The entire contents of which are hereby incorporated by reference herein.

TECHNICAL FIELD OF THE INVENTION

The present invention relates to cell culture in bioreactors, such as flexible cellbag bioreactors. More specifically the invention relates to a process that will support the generation of clinical scale cell product through an initial semi-static culture using a single non-static cell culture platform from start to finish.

DESCRIPTION OF RELATED ART

Adoptive T cell therapies are the most recent personalised medicine to show signs of therapeutic value to patients, predominantly tumour-infiltrating T cells and genetically-modified T cells. T cell therapies are known to have unique culturing requirements, which vary depending on the type of T cell product.

Known protocols for expansion of clinically relevant T cells require an initial stage of cell to cell contact which promotes T cell stimulation and further proliferation. To facilitate the required interactions for cell to cell contact, minimal movement of the cell suspension is deemed to be a necessity and static culture using flasks or static culture bags placed in an incubator are typically used for this stage of the process. In this context, Somerville and Dudley (2012 OncoImmunology; 1(8): 1435-1437) note that non-static bioreactors such as the Xuri™ (GE Healthcare, previously known as Wave™) bioreactor present a challenge for process development including this static step which requires cells to remain in extended physical contact. In a similar way, Rooney et al. (J Immunother 2010; April: 33(3): 305-315) note that antigen-specific cytotoxic T lymphocytes (CTL) have strict requirements for cell to cell contact and have proved difficult to consistently adapt to moving cultures since production of functional cells is best under static culture conditions.

T cells in vivo are activated and induced to proliferate when the T cell receptor (TCR) on T cells is engaged by the antigen-major histocompatibility complex (MHC) on the antigen presenting cells (APC) along with a second costimulatory signal. In response to activation, T cells undergo physical, biological and phenotypic changes including for example increased cell size and secretion of cytokines. This immune response can also be imitated ex vivo by the binding of T cells to co-immobilised anti CD28 and anti CD3 monoclonal antibodies, either onto beads or other surfaces such as the bottom of a culture flask. Proliferatory signals have also been provided by contacting the T cell population with an engineered mammalian cell line expressing the stimulatory factors. In common to all the various methods available for antigen stimulation of T cells for cell culture, is the need for proximity between the T cells and the co-stimulatory signals delivered by either APCs or antibodies, as well as conditions enabling this interaction for an extended period of 1-5 days.

The use of culture flasks and static culture bags is widespread and applied by researchers when doing process development work within the cell therapy field. These simple culture vessels fulfil the requirements in the lower range of working volumes, which can handle small cell numbers, and require standard laboratory equipment. The static culture methods support extended physical cell contact that can promote T cell stimulation and activation. As the cells proliferate, additional culture vessels are required and the number of vessels and cell suspension volume increase by time, e.g. it is possible to go from 50 ml up to ≥20 L or more in the space of 30 days. Such a workflow requires highly qualified personnel and time, and is cumbersome as multiple vessels need to be manipulated. The risk of contamination and human error also increase by time as the number of culture vessels increases.

When trying to adapt the protocol to a more automated and contained process for production of a regulatory compliant cellular immunotherapy, the number of bioreactor systems available for this application is limited. Various bioreactor systems, such as rocking platforms, have been evaluated by several clinical research groups. They have been considered to support the standardisation and scale up of cell therapy clinical production processes and can facilitate the implementation of these processes into phase III clinical trials. Nevertheless, many of these bioreactors do not support the critical cell to cell interactions required in the initial T cell stimulation steps.

When preparing for a clinical phase I/II study the protocol has to be industrialised and scaled-up to enable the generation of sufficient material to reach a therapeutic dose, and also the treatment of 10-20 patients, all under good manufacturing practice (GMP) requirements. Furthermore, to enable regulatory compliant generation of sufficient product material and to supply this material for a much larger cohort, which would be the case in a phase III study (hundreds or thousands of patients), the production process often needs drastic manipulations of the protocol.

Sadeghi et al (2011 J Immunol Methods .364: 94-100) reported that rapid expansion of tumour-infiltrating lymphocytes (TILs) can be directly initiated in a bioreactor system without pre-activation and expansion in T-flasks. TILs are obtained from a tissue biopsy, which can itself act as an antigen so that antigen is already present. The requirements for an initial static phase are therefore different when starting a cell culture with a tissue biopsy as compared with a T cell suspension. Sadeghi et al but also noted that in order to successfully initiate rapid expansion of TILs in higher volumes, activation and pre-expansion in flasks or gas-permeable bags is required.

There is therefore a desire for improved methods for the generation of a clinical scale of cell product, particularly where the cell culture process begins with a suspension of cells requiring a separate antigen stimulus.

SUMMARY OF THE INVENTION

In one embodiment the present invention provides a method comprising:
   (i) inoculating cells into a non-static bioreactor;
   (ii) adding an antigen stimulus to said non-static bioreactor;
   (iii) adding at least a cell growth co-factor to said non-static bioreactor;
   (iv) expanding said cells to result in a clinically relevant cell product;

wherein step (ii) is carried out wherein said non-static bioreactor is kept at a first rocking rate;

and wherein step (iv) is carried out wherein said non-static bioreactor is kept at a second rocking rate which is higher than said first rocking rate.

Being able to utilize a bioreactor system for all aspects of the culturing process is a significant advantage as the cells are contained in a single vessel, which reduces the number of open manipulations required and therefore reduce the chance of contamination of the product.

In another embodiment, the present invention relates to use of a non-static bioreactor in the method of the invention.

In another embodiment, the present invention provides a kit comprising instructions for carrying out the method of the invention.

The definitions and particular embodiments defined hereunder for the method of the invention are equally applicable for the use and kit of the invention.

The present invention represents an optimised procedure using a non-static bioreactor from start to finish for the generation of an expanded cell culture from a suspension of cells exposed to an antigen stimulus. The method of the invention eliminates the requirement for multiple open static systems as used in known methods. An advantage of the present invention is that it provides an alternative semi-static approach that allows the scale-up of cell culturing process in an automated closed environment. The approach can also be adapted to a variety of cell culture procedures that require extended static contact steps during the culture period.

DETAILED DESCRIPTION OF THE PREFERRED EMBODIMENTS

To more clearly and concisely describe and point out the subject matter of the claimed invention, definitions for specific terms used throughout the present specification and claims as well as exemplary embodiments of the invention are provided hereinbelow. Any exemplification of specific terms herein should be considered as a non-limiting example.

The term "inoculating" as used herein refers to the transfer of a relatively small quantity of cells into a cell culture vessel for the purposes of initiating a cell culture. In one embodiment the small quantity of cells is a suspension of cells. In one embodiment the small quantity of cells is not derived from a piece of tissue such as a tissue biopsy. The term "cell culture vessel" can include cell culture flasks, bags, bioreactors of various kind, or scaffolds well known to those of skill in the art. In one embodiment the quantity of cells transferred for a culture of T cells is around $1\times10^6$ to $2\times10^6$ cells per mL. In one embodiment, the inoculating step can be carried out prior to initiating any rocking of the bioreactor. In one embodiment, the inoculating step can be carried out at the first rocking rate as defined herein.

The term "cells" in the context of the present invention can be understood to encompass any cell type that can be used in a cell therapy application. Such cells are sometimes referred to as advanced therapy medicinal products (ATMP). The term "cell therapy application" means any therapy wherein autologous or allogenic cellular material is administered, typically by injection, into a patient and includes such procedures as adoptive immunotherapy or autologous or allogenic transplantation. In the context of the present invention the cellular material is manipulated prior to administration so that the cells express a desired phenotype. So, for example adoptive immunotherapy (also referred to as "adoptive cellular therapy") is a treatment used to help the immune system fight diseases, such as cancer and infections with certain viruses. As per the NCI (National Cancer Institute) definition of adoptive immunotherapy, T cells are collected from a patient and isolated and expanded ex vivo in the laboratory, which increases the number of T cells that are able to kill cancer cells or fight infections. These T cells are given back to the patient to help the immune system fight disease.

Figure 1:
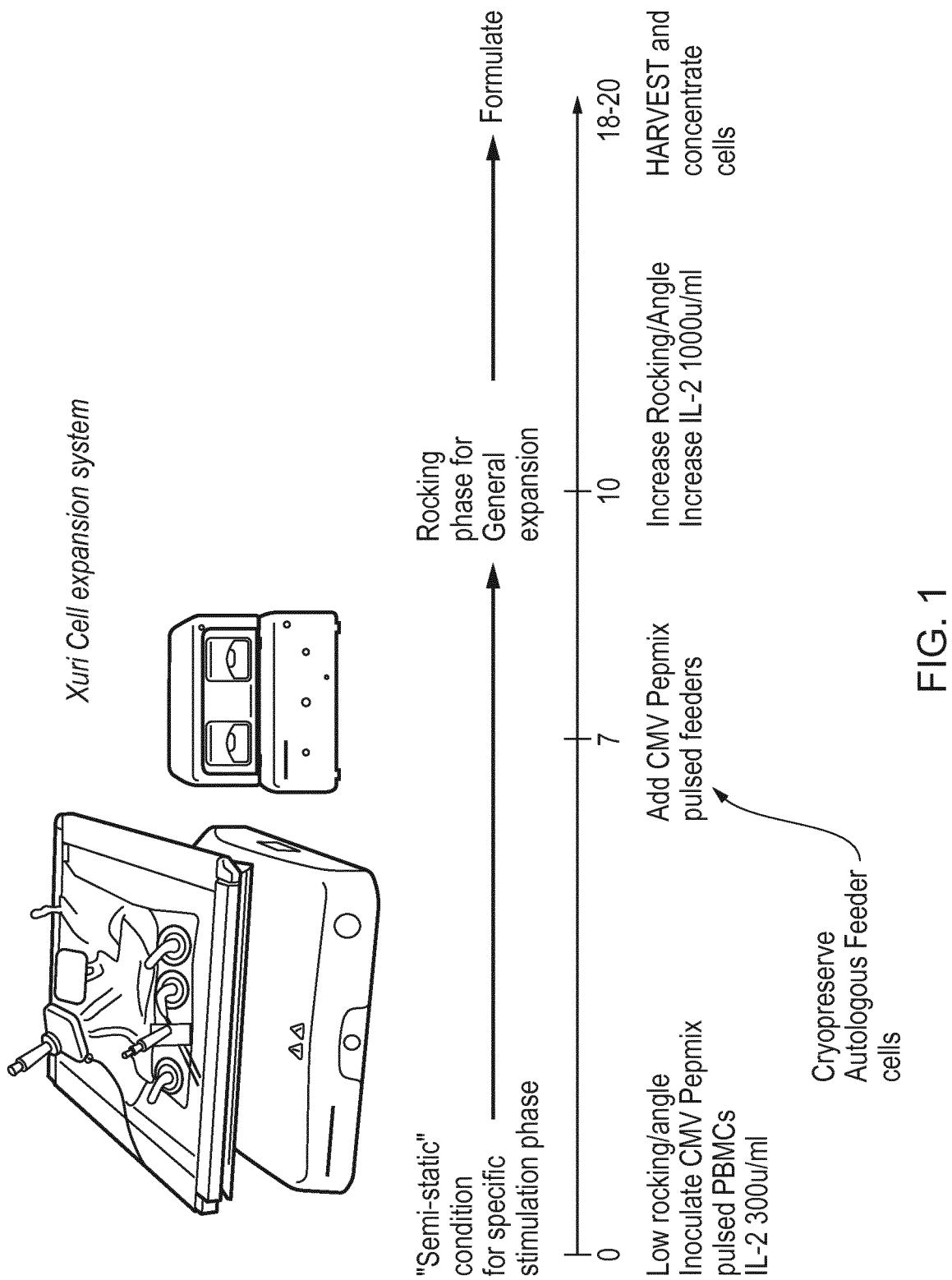
FIG. 1 shows a general workflow for the production of antigen-specific T cells (ASTs) directly in the Xuri™ Cell expansion system.

A "non-static bioreactor" in the context of the present invention is a device or system configured to grow a cell culture wherein the device confers movement on the cell culture to facilitate its growth. Suitably, the method of movement is not damaging to the cells, e.g. induces little to no shear force or grinding force on the cell culture. Non-liming examples of movement include shaking, stifling and rocking. In one embodiment of the invention the movement is rocking. Examples of commercially-available non-static bioreactors include the Xuri™ (GE Healthcare), Biostat™ RM (Sartorious), and XRS 20 Bioreactor (Pall). FIG. 1 shows a general workflow for the production of antigen-specific T-cells (ASTs) directly in the Xuri™ Cell expansion system according to an embodiment of the invention.

An "antigen stimulus" is a factor which induces white blood cells to undergo physical, biological and phenotypic changes. The antigen stimulus can be understood to induce a certain sub-population of cells having a particular phenotype/specificity to become a more dominant part of the cell population. Non-limiting examples include antigenic peptides, or tumour lysate, which can be processed by artificial antigen-presenting cells (APCs) and presented on a MHC for the TCR engagement or APCs to present the peptide on a MHC complex for a TCR. One known example of the latter embodiment is to co-culture PBMCs with gamma-irradiated autologous EBV-transformed lymphoblastoid cell lines (EBV-LCLs) to obtain EBV-specific CTLs.

The term "cell growth co-factor" refers to factors that promote the expansion of the cells. They are added to the non-static bioreactor either in solution or attached to a solid surface such as beads.

In one embodiment examples of cell growth co-factors include anti CD28 and/or anti CD3 monoclonal antibodies, either co-immobilised on beads or other surfaces such as the bottom of a culture flask, or added in solution, or an engineered mammalian cell line expressing the stimulatory factors such as K562 cell line expressing CD28/CD3. EP1594958B1 describes a known method to stimulate T cells with beads having bound anti CD3 and CD28. In one embodiment, the cell growth co-factors of this embodiment are added in the method of the present invention at the first rocking rate and prior to the expanding step (iv).

In one embodiment the cell growth co-factor is a cytokine or a cocktail of cytokines. Non-limiting examples of cytokines include interleukin-2 (IL-2), interleukin-4 (IL-4), interleukin-7 (IL-7), interleukin-12 (IL-12), interleukin-15 (IL-15) and interleukin-21 (IL-21) as well as mixtures thereof. In one embodiment a cocktail of cytokines might include a mixture of IL-4 and IL-7, or a mixture of IL-2 and IL-7 and/or IL-15 and IL-21. In one embodiment, the cell growth co-factors of this embodiment are added in the method of the present invention at the first rocking rate and prior to the expanding step (iv) and/or the cell growth co-factors of this embodiment are added during the expanding step (iv) of the method of the invention at the second rocking rate.

The term "expanding" in the method of the invention refers to the process of increasing the number of cells in a cell culture. In the expanding step cells are fed and culture media is replaced at regular intervals, in one embodiment according to a feed regimen. The specific timings and amounts of media added in a particular feed regimen will depend on the cell number and the levels of metabolites in the culture.

A "clinically relevant cell product" is one that can be used in a cell therapy application. The clinically relevant cell product shall be suitable for clinical use. In other words, it should meet the specific requirements of a medicinal product as defined in the approval made by international and/or national regulatory bodies, e.g., the product should be sterile and have an endotoxin level below 0.5 EU/kg. The term "clinical use" refers to use of a pharmaceutical product by individual subjects/patients. The term "pharmaceutical product" encompasses the clinically relevant cell product of the invention and can be understood to refer to a pharmaceutically acceptable composition of a pharmaceutically active substance intended for administration to a patient. Clinical use can be understood to include the use of a pharmaceutical product in Phase I, II and III clinical trials and the use of the product in patients in clinical practice. In one embodiment the clinically relevant cell product is suitable for use in clinical trials. Enough cells should be generated to reach therapeutic dose and carry out quality control analysis, and this production process could be done for one patient at a time, multiple in parallel or staggered. A range of $10^7$-$10^{15}$ cells in the cell product of one batch can be suitable. In any study a suitable method enables the generation of sufficient material to reach a therapeutic dose for each of the patients in the study, all under good manufacturing practice (GMP) requirements. The number of subjects to treat varies depending on the phase of the study, as is well known to those of skill in the art. For a phase III study the number of patients can reach hundreds or even thousands.

The method of the invention can in one embodiment be understood to be divided into two modes of operation; the semi-static culture, and a rapid expansion protocol. The term "semi-static culture" can be understood to refer to those steps of the method of the invention carried out at said first rocking rate, i.e. performing culture procedures requiring cell interactions, promoting activation and growth of said cells in a non-static bioreactor, under a period of time necessary for physiological changes to occur of the said cells. The "rapid expansion protocol" includes those steps carried out at said second rocking rate, i.e. the feed regimen to optimize and stimulate the growth of said cells, subsequent to semi-static culture mode of operation, when cell to cell interactions is less critical.

The "first rocking rate" a semi-static rate of movement used for those steps of the method wherein in known methods a static state is used. In one embodiment said first rocking rate is a speed no greater than 4 rpm and at an angle of no greater than 4 degrees. In one embodiment the first rocking rate is between 2-4 rpm and at an angle between 2-4 degrees. In one embodiment the first rocking rate is 2 rpm and at an angle of 2 degrees.

Since near proximity between said cells and the growth stimulatory factors is necessary to induce activation and expansion, starting cell density (cells/mL) is recommended to be kept at certain level. A non-limiting example of recommended cell density is ≥$10^6$ viable cells/mL. Normally, when expanding human cells ex vivo the starting population is small, thus requiring initial low culture volume to enable the recommended cell density. A non-limiting examples of a low starting volume is ≥250 ml in a 2 L Cellbag.

In one embodiment the method of the invention further comprises means to control evaporation and/or condensation and/or accumulation of waste metabolites (hereunder also referred to as "means to control"), in particular at stages of low culture volumes. In one embodiment, said means to control is applied during the semi-static culture mode as described hereinabove. In one embodiment said means to control is applied at the early stages of the method of the invention, e.g. steps (i)-(ii) or steps (i)-(iii).

In one embodiment said means to control comprises thermal insulation. In one embodiment thermal insulation is achieved using the lid of the bioreactor. In another embodiment said thermal insulation is achieved by wrapping the cell bag in a suitable insulating material. In one embodiment said insulating material is aluminium foil. In one embodiment where the Xuri™ W5 is used a plate riser can be inserted in the tray of the system to enable correct temperature reading.

In one embodiment said means to control comprises controlling the gas flow rate. In one embodiment said gas flow rate is controlled to 0.05-0.1 litres per minute (LPM). In one embodiment said gas flow rate control is applied during the first 3-4 days.

In one embodiment said means to control comprises daily medium additions. In one embodiment said daily medium additions are carried out in the initial days. In one embodiment said medium additions result in a total volume on day 5 of >40% of the maximal working volume without diluting the cell density below the minimum number/ml required. In one embodiment said daily medium additions are carried out slowly to keep the temperature above a critical level, e.g. from day 2-3; the daily medium shots can in one embodiment be ≤50-100 ml in cultures where the starting volume is 300 ml. In one embodiment the addition of medium can be performed so that the temperature drop is ≤1° C. from the setpoint In one embodiment said means to control comprises perfusion added during the early stages to avoid high osmolality (200 ml/day) at a total volume lower than 1 L. An example of appropriate volumes in a 2 L culture vessel is 400-500 ml and a recommended minimum cell density is ≥$0.8\times10^6$ cells/ml. Besides media addition, perfusion can also be considered during the early stages if high osmolality and waste metabolites accumulated in the culture. Mainly because accumulation of waste metabolites could be detrimental to the culture and eventually affect their proliferation rate at later stages. Perfusion rate can be ≤200 ml/day (in ≤25 ml shots for a shot-based perfusion in a Xuri™ W5 system) to keep temperature constant and facilitate temperature control. "Rapid expansion protocol" (REP) is applied when the cell to cell interactions is less critical and the said cells has been activated or undergone a physical change during the semi-static culture. The second rocking rate is applied, and an increased gas flow, perfusion regimen not limited by temperature but by cell concentration and culture volume. A non-limiting example of increased gas flow into the bioreactor is ≥0.1-0.6 LPM.

The "second rocking rate" is used during step (iv) of the method of the invention when the cells are expanding. The second rocking rate can be varied throughout the expanding step (iv) as a function of the quantity of cells in the cell culture, i.e. where there are more cells the second rocking rate can be higher. In one embodiment the second rocking rate is a speed greater than 4 rpm and at an angle of greater than 4 degrees. In one embodiment said second rocking rate is up to 25 rpm and at an angle of up to 15 degrees. In one embodiment said second rocking rate is up to 15 rpm and at an angle of up to 15 degrees. In one embodiment said second rocking rate is up to 10 rpm and at an angle of up to 10 degrees. In one embodiment, second rocking rate is 4-8 rpm and an angle of 4-6 degrees for cell densities of <$2^6$ cells/ml and with volumes <1 L. In one embodiment the second rocking rate is between 8-10 rpm and an angle of 6 degrees for >$2^6$ cells/ml and volume >1 L. In one embodiment for cell densities of >$15^6$, the second rocking rate is 10-15 rpm and an angle of 6 degrees.

The method of the present invention provides a useful development as compared with known processes as it limits open handling, reduces risks for contamination and promotes a more efficient workflow.

Figure 2:
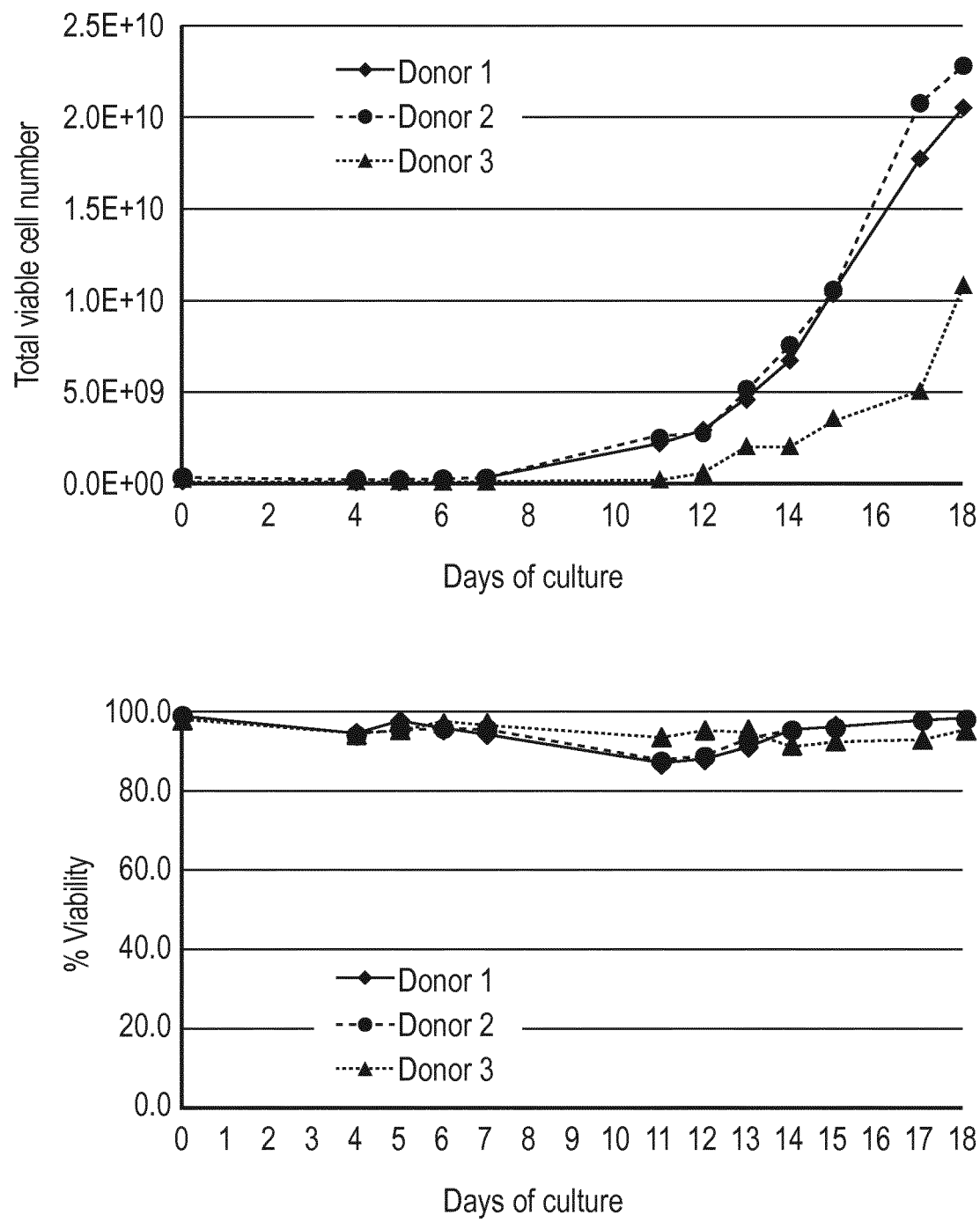
FIG. 2 shows total cell numbers (top) and percentage viability (bottom) of cells grown in the Xuri™ bioreactors. Cells from donor 1 were cultured in Xuri™ W25 systems, and donor 2 and 3 in Xuri™ W5 systems.
Figure 3:
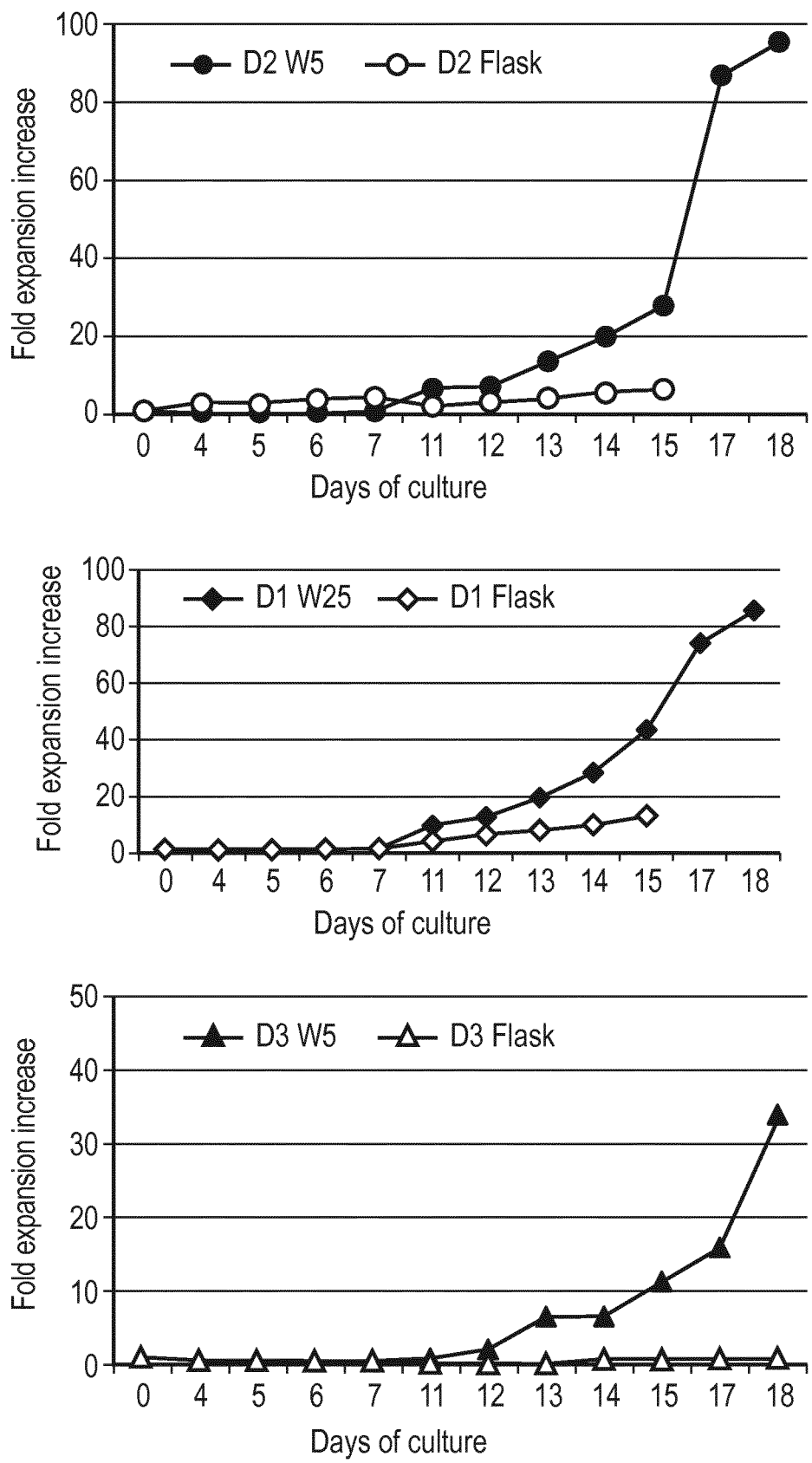
FIG. 3 illustrates the fold increase in cell number throughout the culture in Xuri™ Cell expansion systems and tissue culture flasks for each of 3 donors.
Figure 5:
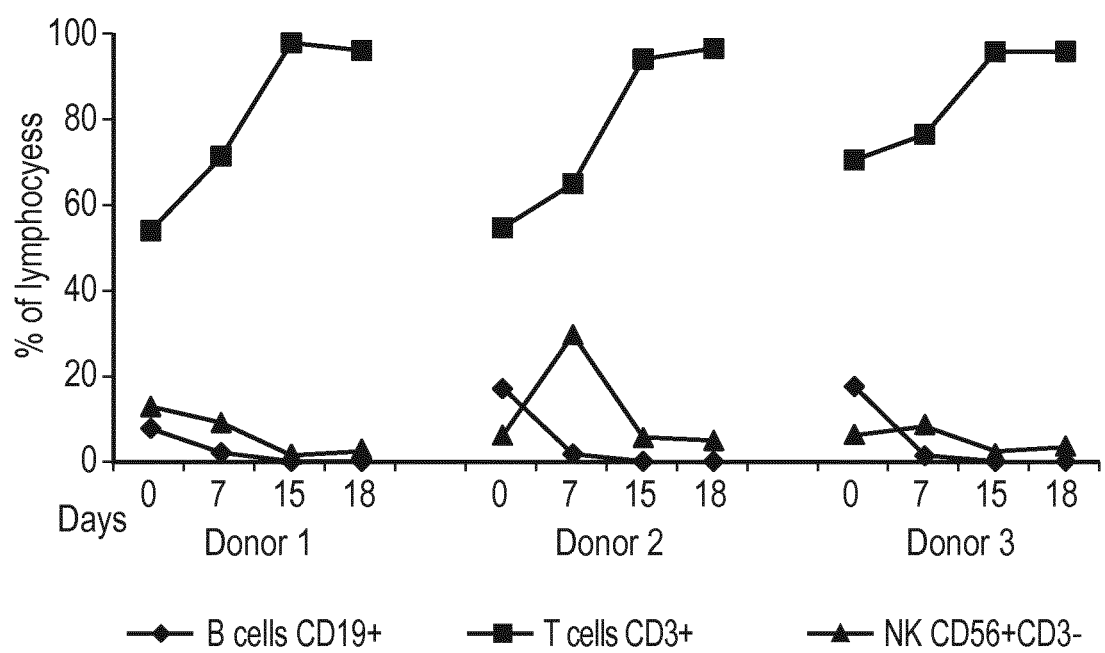
FIG. 5 illustrates the frequency of the peripheral blood lymphocyte populations throughout the culture period in the Xuri™ systems. The number of positive cells was determined by flow cytometry (FACS Fortessa). Lymphocytes were gated based on their forward and side scatter profile. % B cells (CD19+), CD3+ T cells, NK (CD56+CD3−) and NKT-like cells (CD3+CD56+) are shown within lymphocyte gate.
Figure 6:
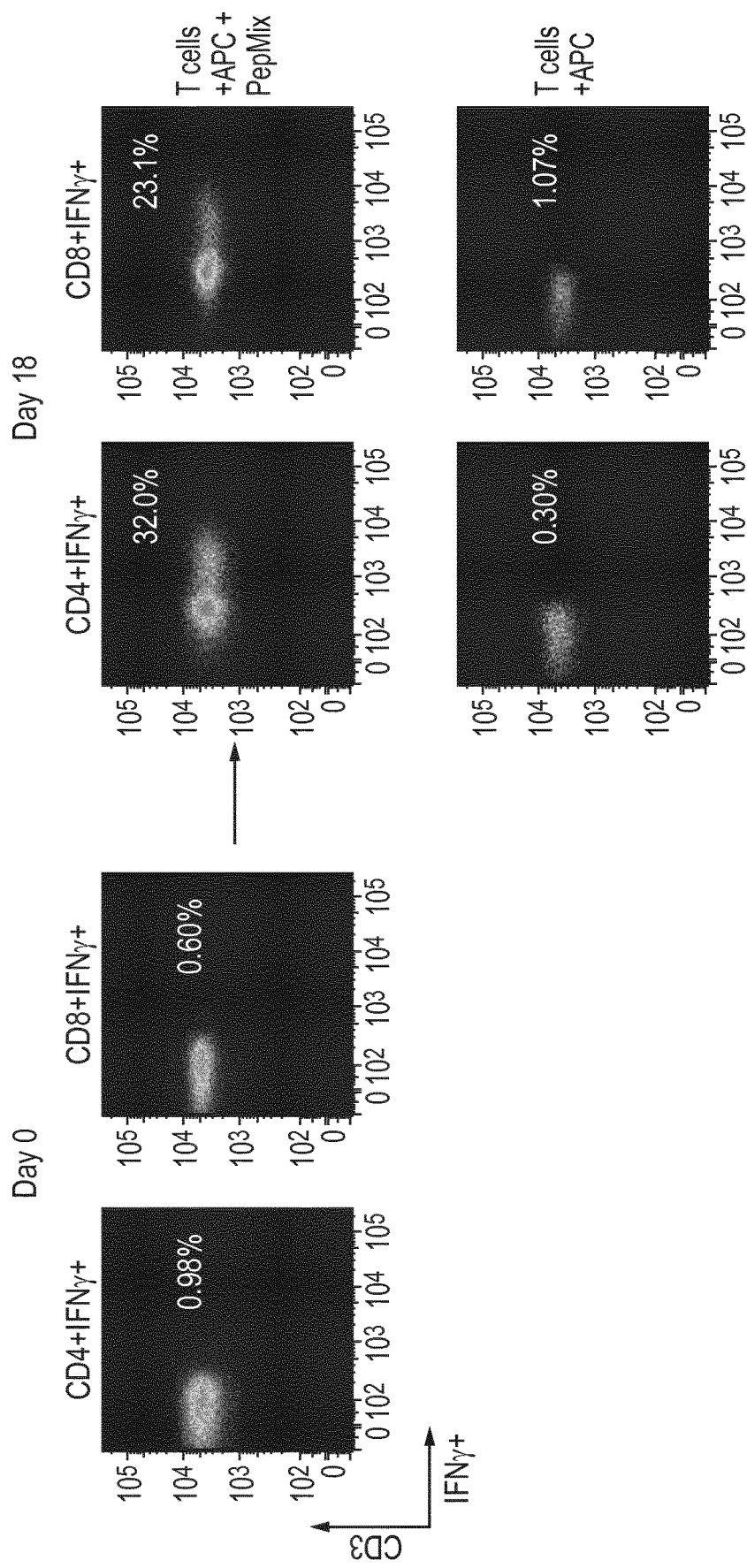
FIG. 6 shows representative flow cytometric plots for IFNγ secretion of CD8+ T cells and CD4+ T cells on day 0 and day 18 for donor 1. T cells were either stimulated with PBMC (APC) alone (Non-specific IFNγ secreting T cells, negative control) or with APC+CMV Pepmixes (Test for specificity).
Figure 7:
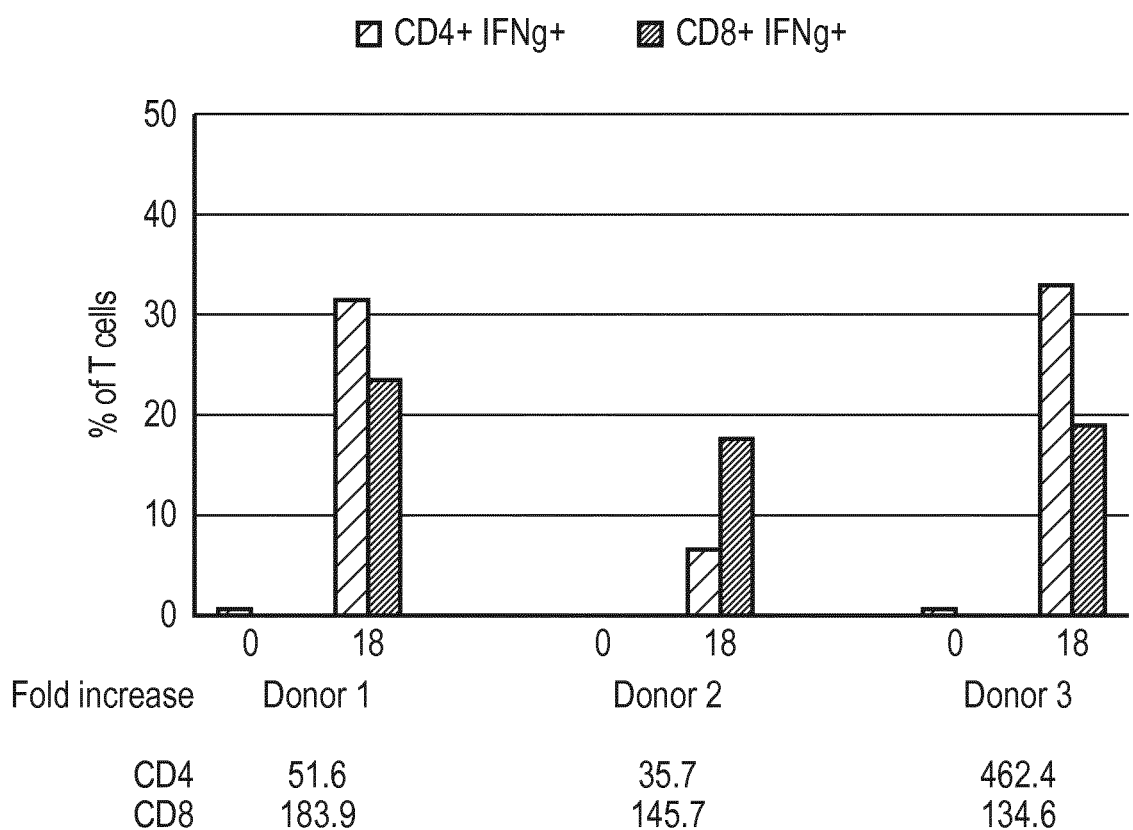
FIG. 7 shows IFNγ secretion of CD8+ T cells and CD4+ T cells throughout the culture in Xuri™ systems. Percentage of CD4+ or CD8+ T cells is shown on the graph and Fold increase in specificity is shown for all the donors below graph. T cells were either stimulated with PBMC alone (Non-specific IFNγ secreting T cells) or with PBMC+CMV Pepmixes (Test for specificity). CMV-specific T cells=(T cells+PBMC+CMV peptide)−(T cells+PBMC).

In one embodiment, a procedure using the Xuri™ Cell expansion platform from start to finish has been developed for the generation of antigen-specific T cells and is described in Example 1. By adapting some crucial steps from conventional protocols to the Xuri™ Cell expansion systems, this process has eliminated the requirement to use multiple open static systems, as would be required with prior methods. Application of Xuri™ Cell expansion systems for generation of ASTs therefore provides an alternative semi-static approach that allows the scale-up of ASTs culturing process in an automated closed environment. Using the semi-static approach, this platform can also be adapted to any other cell culture procedures that require extended static contact steps during the culture period. Example 1 demonstrates that a non-static bioreactor supports growth of T cells with a higher fold increase in cell number, compared to traditional tissue culture flasks (FIGS. 2, 3 and 5). Expansion of T cell cultures containing high antigen specificity against CMV was achieved for all donors using the Xuri™ cell expansion systems (with >35 fold-increase of specificity, ranging from 35.7 to 462.4 and 134.6 to 183.9 fold-increase for CD4+ T cells and CD8+ T cells, respectively; see FIGS. 7 and 8).

Brief Description of the Examples

Example 1 describes expansion of clinically relevant antigen specific T cells using the Xuri™ platform. Fresh peripheral blood mononuclear cells (PBMC) from three healthy donors were pulsed with HCMVA Pepmixes (PM-IE1 and PM-pp65) and inoculated directly into a Cellbag on the Xuri™ cell expansions system W5 or W25 with a very gentle rocking/angle. After 7 days, the cell cultures were re-stimulated with irradiated autologous Pepmixes-pulsed PBMC. On day 10/11 the rocking was increased to promote the expansion phase. Cell cultures for both donors were set up concurrently in tissue culture flasks as a comparison to the semi-static cultures.

List of Abbreviations Used in the Examples

CMV cytomegalovirus
DMSO dimethyl sulfoxide
hr(s) hour(s)
PBMC(s) peripheral blood mononuclear cell(s)
rpm revolutions per minute

EXAMPLES

Example 1. Expansion of Clinically Relevant Antigen Specific T Cells Using the Xuri™ Platform Materials & Methods Fresh peripheral blood mononuclear cells (PBMC) from three CMV seropositive healthy donors were isolated using Ficoll-Paque PLUS medium (GE Healthcare). A portion of the PBMC were kept for initiation of culture and the remaining of cells were cryopreserved in 90% heat-inactivated human serum (TCS Biosciences)+10% DMSO (Sigma) for later use as autologous feeders.

A starting cell number of 350E6 cells were re-suspended in 10 mls complete medium: X-VIVO medium (Lonza) supplemented with 5% heat-inactivated human serum, 2 mM GlutaMAX 1-glutamine (Life Technologies), 100 U/ml penicillin (Life Technologies) 100 µg/ml streptomycin (Life Technologies) and 300 units/ml IL-2 (Ge Healthcare). The cells were pulsed with HCMVA Pepmix PM-IE1 (JPT) and HCMVA Pepmix PM-pp65 (JPT) at 10 ng/15E6 cells for 2 hrs at 37° C.

A Cellbag™ bioreactor (GE Healthcare) was placed on either a Xuri™ Cell Expansion System W5 or W25 (GE Healthcare), filled with 5% $CO_2$ and a reservoir containing complete media and a waste bag was connected. An initial volume 200-250 mls complete media was added to the Cellbag™ and allowed to equilibrate to 37° C. for 2 hrs.

After 2 hrs, 300E6 of the peptide-pulsed cells were inoculated into the Cellbag™ and additional media added, giving a total of 300 mls with 1E6 cells/ml per Cellbag™. The cells were cultured in semi-static conditions of 2 rocks per minute at a 2° angle and gas flow rate of 0.05 LPM. To minimise evaporation of the culture media during the semi-static phase of the culture the Cellbags™ were either wrapped in aluminium foil (for the Xuri™ Cell Expansion System W5) or the lid of the instrument was used (for the Xuri™ Cell Expansion System W25). Once initiated, the cultures in the Cellbags™ were left undisturbed for 3 days to allow cell to cell interactions to occur.

A traditional static culture was set up in parallel as a comparison to the semi-static culture. 50E6 cells were re-suspended in 50 mls (1E6/ml) and cultured in a flask at 37° C. in an incubator. From day 3 fresh media was added to the Cellbags™, reaching 400 mls-500 mls by day 7. Daily sampling was performed for cell counting and for biochemical analysis (Lactate, ammonium, glucose, pH). The flasks were fed batch with similar proportional volumes. From day 5-6 rocking/angle was increased to 4 rocks per minute and an angle of 4 degrees until day 7. 24 hrs before the addition of feeders for re-stimulation, 200 ml of media was perfused to control lactate, ammonium and glucose levels. The same perfusion rate was performed manually for the flasks by centrifugation.

Figure 4:
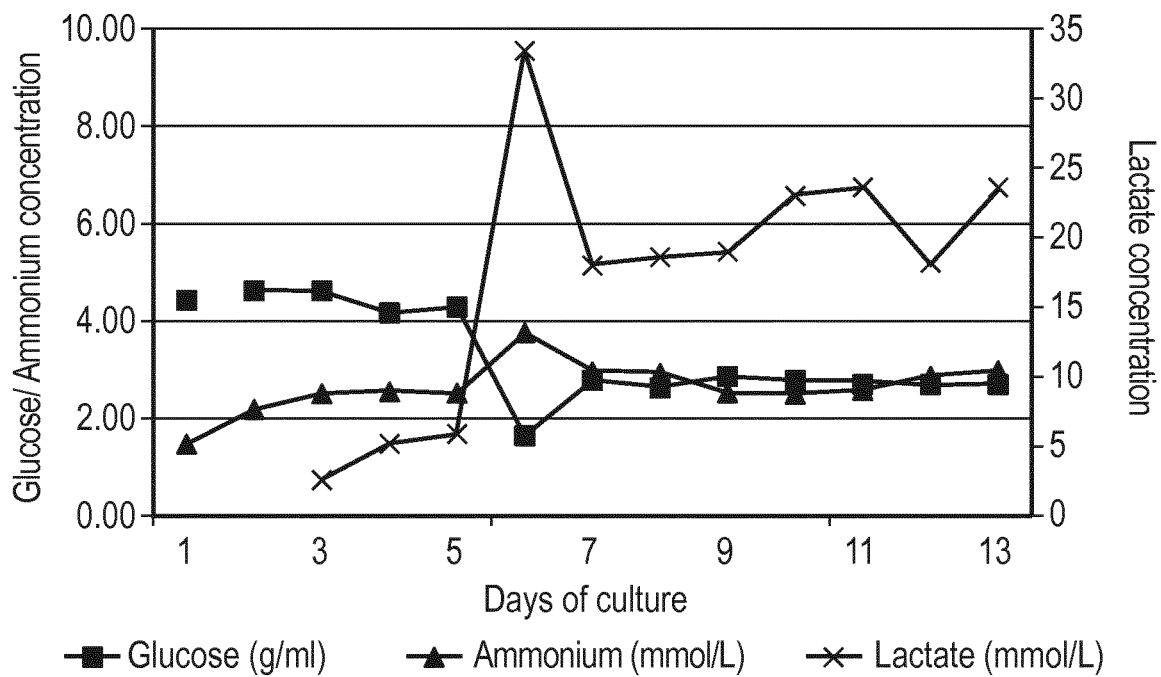
FIG. 4 (top) shows levels of metabolites glucose (g/L), lactate (mmol/L), and ammonium (mmol/L) and FIG. 4 (bottom) shows total volume and perfusion rates (bottom) for culture in the Xuri™ system. Representative data is shown for culture from Donor 1 in the Xuri™ W25 system.
Figure 4:
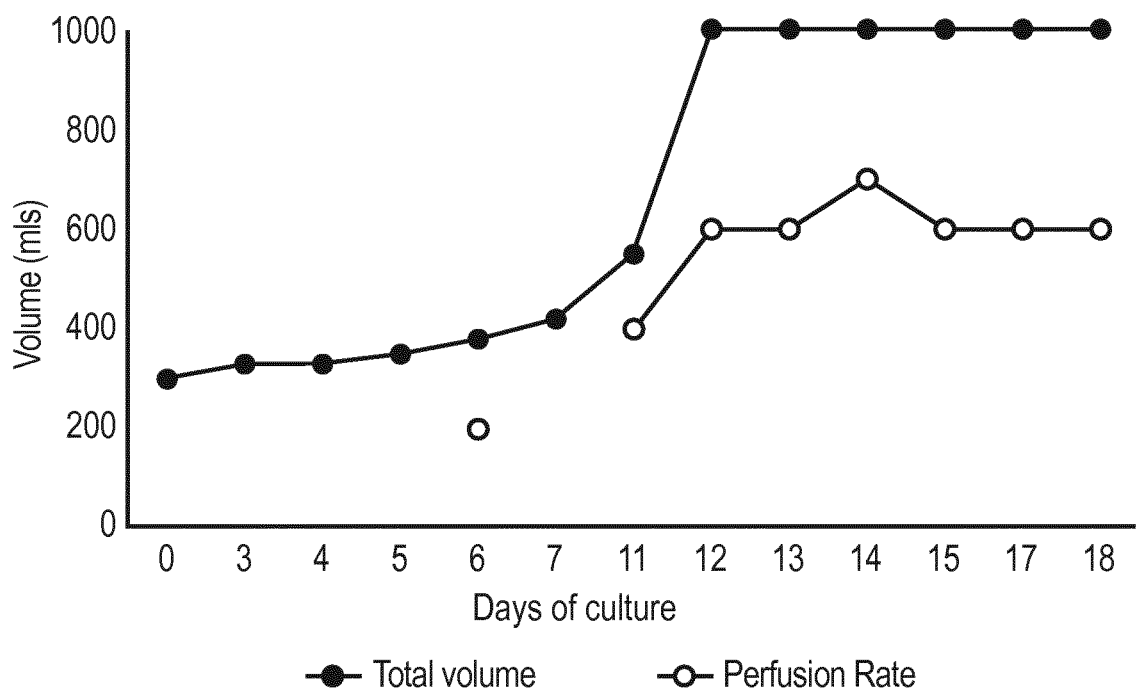

On day 7 the cultures were re-stimulated with autologous peptide-pulsed feeders. Cryopreserved autologous PBMCs were thawed in complete media, irradiated at 30Gy and pulsed for 2 hrs with the Pepmixes (10 ng/15E6 cells). The cells were added to the Cellbag™ and flask cultures at a ratio of 1:1 feeders to T cells. The cultures were incubated for 3 days without interference at 2 rpm at a 2° angle, From day 10 Cellbags™ were fed batched to maintain at least 1E6/ml until the maximum volume of 1 L was obtained. Thereafter, a perfusion rate of 200-700 mls per 24 hrs was adjusted according to the metabolite readings to control glucose and waste metabolites lactate and ammonium (see FIG. 4). The same proportional media additions were performed in the flasks until the volume reached 100 mls and manual perfusions were carried from day 10 every 2 days. Daily monitoring, cell counts and biochemical analysis were carried. From day 11 the rocking/angle was increased gradually every day to 4 rpm/4°, 8 rpm/6°, 10 rpm/6° (2-20E6 cells/ml) and 12 rpm/6o if the cells are >20E6/ml.

Phenotypic Analysis

Samples for flow cytometry analysis were taken and cryopreserved on day 0, 7, 15 and 18. Cells were thawed and stained with antibody panels detecting immunophenotypic markers for lymphocyte populations. $1\times10^6$ cells were stained with CD3-PerCP™ Cy™5.5 (BD™ Biosciences), CD4-V500 (BD™ Biosciences) or -PE (BD™ Biosciences), CD8-Alexa Fluor™ 488 (BD™ Biosciences) together with CD56-PE (BD™ Biosciences) and CD19-APC (BD™ Biosciences).

For analysis of cytokine expression the cells were divided into negative control (Cells+PBMC), and test for specificity (Cells+PBMC+Pepmixes). These were incubated overnight at 37° C. Cytokine secretion assay was carried out to test for antigen specificity using the MACs IFN Secretion assay detection kit, according to manufacturing instructions (Miltenyi Biotec).

The stained cells were analysed on FACSFortessa flow cytometer using FACSDiva™ software, according to the manufacturer's instructions (BD™ Biosciences).

The invention claimed is:

1. A method comprising:
   (i) inoculating cells in a suspension into a non-static bioreactor;
   (ii) adding an antigen stimulus to said cells in said suspension in said non-static bioreactor kept at a first rocking rate no greater than 4 rpm and at an angle of no greater than 4 degrees;
   (iii) adding at least a cell growth co-factor to said non-static bioreactor;
   (iv) expanding said cells to result in a clinically relevant cell product in said non-static bioreactor kept at a second rocking rate which is higher than said first rocking rate and at an angle of greater than 4 degrees, wherein the second rocking rate is (a) between 4-8 rpm and an angle of 4-6 degrees for cell densities of $<2^6$ cells/ml and with volume less than 1 L, and (b) between 8-10 rpm and an angle of 6-15 degrees for $>2^6$ cells/ml and volume greater than 1 L;
   wherein said cells are leucocytes.

2. The method of claim 1 wherein steps (ii) and (iii) are repeated one or more times during step (iv).

3. The method of claim 1 wherein said leucocytes are selected from the group comprising lymphocytes, monocytes or cells derived from monocytes.

4. The method of claim 1 wherein said leucocytes are peripheral blood mononuclear cells (PBMCs).

5. The method of claim 1 wherein said non-static bioreactor comprises a flexible cell bag.

6. The method of claim 1 wherein said antigen stimulus comprises antigenic peptides or tumour lysate.

7. The method of claim 1 wherein said step of expanding said cells comprises replacing a culture medium in the suspension at regular intervals.

8. The method of claim 1 wherein said cell growth co-factor comprises anti-CD28 and/or anti-CD3 monoclonal antibodies.

9. The method of claim 8 wherein said cell growth co-factor is added prior to the expanding step (iv).

10. The method of claim 8 wherein said cell growth co-factor is a cytokine or a cocktail of cytokines.

11. The method of claim 10 wherein said cytokine is selected from interleukin-2 (IL-2), interleukin-4 (IL-4), interleukin-7 (IL-7), interleukin-12 (IL-12), interleukin-15 (IL-15) and interleukin-21 (IL-21).

12. The method of claim 10 wherein said cell growth co-factor is added prior to the expanding step (iv).

13. The method of claim 10 wherein said cell growth co-factor is added at regular intervals during said expanding step (iv).

14. The method of claim 1 wherein said clinically relevant cell product comprises antigen-specific T cells, regulatory T cells or genetically-modified PBMCs.

15. The method of claim 14 wherein said clinically relevant cell product comprises antigen-specific T cells or genetically-modified PBMCs.

16. The method of claim 14 wherein said antigen-specific T cells are cytotoxic virus-specific T cells or tumour-specific T-cells.

17. The method of claim 14 wherein said genetically-modified PBMCs comprise chimeric antigen receptor (CAR) T cells or TCR-modified T cells.

18. The method of claim 1 wherein said first rocking rate is between 2-4 rpm and at an angle between 2-4 degrees.

19. The method of claim 1 wherein the non-static bioreactor comprises means to control evaporation and/or condensation and/or accumulation of waste metabolites.

20. The method of claim 19 wherein said means to control comprises thermal insulation.

21. The method of claim 19 wherein said means to control comprises controlling a gas flow rate of gas supplied to the non-static bioreactor.

22. The method of claim 19 wherein said means to control comprises daily medium additions.

23. The method of claim 1, wherein the wherein the second rocking rate is between 8-10 rpm and an angle of 6 degrees for >$2^6$ cells/ml and volume greater than 1 L.

* * * * *